United States Patent
Troxler et al.

(10) Patent No.: US 6,861,430 B2
(45) Date of Patent: Mar. 1, 2005

(54) β-CARBOLINE DERIVATIVES AND ITS PHARMACEUTICAL USE AGAINST DEPRESSION AND ANXIETY

(75) Inventors: Thomas J. Troxler, Wahlen (CH); Konstanze Hurth, Saint Louis (FR); Daniel Hoyer, Huningue (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/472,630
(22) PCT Filed: Apr. 2, 2002
(86) PCT No.: PCT/EP02/03624
§ 371 (c)(1), (2), (4) Date: Sep. 19, 2003
(87) PCT Pub. No.: WO02/081471
PCT Pub. Date: Oct. 17, 2002

(65) Prior Publication Data
US 2004/0132735 A1 Jul. 8, 2004

(30) Foreign Application Priority Data
Apr. 3, 2001 (GB) .............................................. 0108337

(51) Int. Cl.⁷ ........................ C07D 471/04; A61K 31/44
(52) U.S. Cl. ............................ 514/252.05; 514/252.06; 514/255.05; 514/256; 514/292; 544/238; 544/333; 544/405; 546/85
(58) Field of Search ................................. 544/238, 333, 544/405; 546/85; 514/252.05, 252.06, 255.05, 256, 292

(56) References Cited
U.S. PATENT DOCUMENTS

| 5,348,958 A | 9/1994 | Kruger et al. ............... 514/249 |
| 6,057,340 A | 5/2000 | Kelly et al. ................. 514/326 |

FOREIGN PATENT DOCUMENTS

WO    WO 99/64420 A    12/1999

OTHER PUBLICATIONS

Poitout L. et al., "Identification of Potent Non–Peptide Somatostatin Antagonists with sst₃ Selectivity", J. Med. Chem.,vol. 44, pp. 2990–3000 (2001).

*Primary Examiner*—Deepak Rao
(74) *Attorney, Agent, or Firm*—E. Jay Wiusz, Jr.

(57) ABSTRACT

The invention provides compounds of formula (I) wherein R1 to R5 are as defined in the description, and their preparation. The compounds of formula (I) are useful as pharmaceuticals.

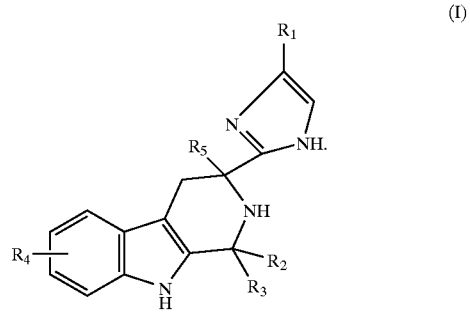

6 Claims, No Drawings

β-CARBOLINE DERIVATIVES AND ITS PHARMACEUTICAL USE AGAINST DEPRESSION AND ANXIETY

The present invention relates to novel β-carboline derivatives, their preparation, their use as pharmaceuticals and pharmaceutical compositions containing them.

More particularly the invention provides a compound of formula I

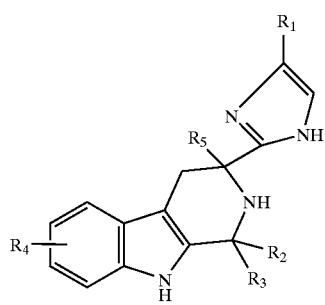

wherein
$R_1$ is a group of formula

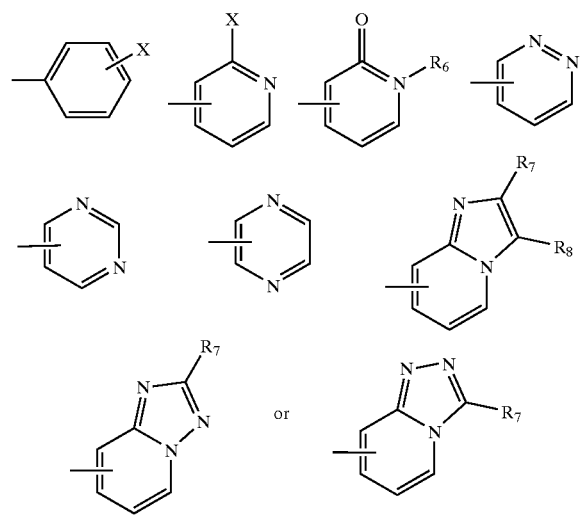

wherein $R_6$ is $(C_{1-4})$alkyl, $R_7$ and $R_8$, independently, are hydrogen or $(C_{1-4})$alkyl and X is hydrogen, $(C_{1-4})$alkoxy, $(C_{1-4})$alkylamino or di$(C_{1-4})$alkylamino, $R_2$ and $R_3$, independently, are $(C_{1-4})$alkoxy$(C_{1-4})$alkyl or $(C_{3-7})$cycloalkyl$(C_{1-4})$alkyl, or, provided $R_1$ is not an optionally substituted phenyl group, $(C_{1-12})$alkyl, $R_4$ is hydrogen, $(C_{1-4})$alkyl, $(C_{1-4})$alkoxy, halogen or trifluoromethyl and $R_5$ is hydrogen or $(C_{1-4})$alkyl, in free base or acid addition salt form.

On account of the asymmetrical carbon atom(s) which is (are) present in the compounds of formula I and their salts, the compounds may appear in optically active form or in form of mixtures of optical isomers, e.g. in form of racemic mixtures. All optical isomers and their mixtures including the racemic mixtures are part of the present invention.

The compounds of formula I and their salts may also appear in the tautomeric forms having the formulae Ia and Ib

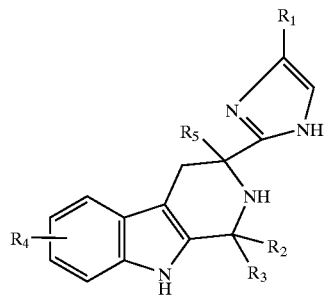

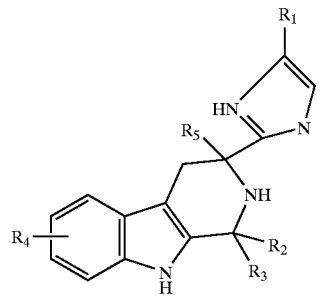

Both tautomatic forms are part of the present invention.

Halogen is fluorine, chlorine, bromine or iodine, preferably fluorine or chlorine. The above-defined alkyl and alkoxy groups preferably represent methyl and methoxy.

In a further aspect, the invention provides a process for the production of the compounds of formula I and their salts, whereby a compound of formula II

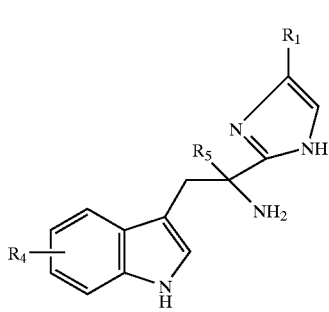

wherein $R_1$, $R_4$ and $R_5$ are as defined above, is reacted with a compound of formula III

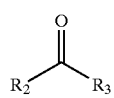

wherein $R_2$ and $R_3$ are as defined above, and the compounds of formula I thus obtained are recovered in free base or acid addition salt form.

The reaction can be effected according to known methods, e.g. as described in Example 1.

Working up the reaction mixtures according to the above process and purification of the compounds thus obtained may be carried out in accordance to known procedures.

Acid addition salts may be produced from the free bases In known manner and vice-versa.

The compounds of formula II and III are known or may be prepared according to known procedures, for example according to WO 99/64420 for the compounds of formula II.

Compounds of formula I and their pharmaceutically acceptable acid addition salts, hereinafter referred to as agents of the Invention, exhibit valuable pharmacological properties when tested in vitro using somatostatin (somatotropin release inhibiting factor, SRIF) receptor expressing cell cultures and in animals, and are therefore useful as pharmaceuticals.

In particular the agents of the invention show high affinity to somatostatin receptors. More particularly they are selective antagonists at somatostatin $sst_3$ receptors, previously called SSTR-3 receptors (see Hoyer et al., TiPS, 1995, 16; 86–88), as determined in radioligand binding and second messenger studies [see for example K. Kaupmann et al., FEBS Letts. 1993, 331:53–59. S. Siehier et al. Naunyn Schmiedeberg's Arch Pharmacol, 1999, 360: 488–499] where they exhibit selective affinity for $sst_3$ receptors with pKd values between about 7.5 and 9.0 and act as antagonists with pKi values of about 7.5 to 9.0 (S. Siehler & D. Hoyer, Naunyn Schmiedeberg's Arch Pharmacol, 1999: 360: 510–521).

The agents of the invention are therefore useful for treatment in anxiety, depression, social phobia, panic disorders, GAD (generalized anxiety disorders), OCD (obsessive compulsive disorders), post traumatic stress disorders, somatoform disorders, personality disorders, ADHD (attention deficit and hyperactivity disorders), bipolar disorders, schizophrenia, including negative symptoms, neurodegenerative diseases such as learning/mlmory disorders, dementia, age associated memory impairment, senile dementia of Alzheimer's type (SDAT), for the treatment of tumours and for vascular disorders and immunological diseases, as confirmed in a range of standard tests as indicated below.

In the social exploration test at doses of about 0.01 to 10 mg/kg p.o., the agents of the invention increase social contact time of rats similarly to classical anxiolytics such as benzodiazepines e.g. chlordiazepoxide or NK1 antagonists (Vassout A, Veenstra S, Hauser K, Ofner S, Brugger F, Schilling W, Gentsch C, Regulatory Peptides. 2000; 96, 7–16).

Furthermore in the mouse intruder test [Triangle, 1982, 21: 95–105; J. Clin. Psychiatry, 1994, 55:9 (suppl. B) 4–7], the agents of the invention increase social investigation and reduce defensive ambivalence in the treated intruder mouse at doses of about 1 to about 10 mg/kg s.c., suggesting an antimanic profile similar to carbamazepine and lithium, a neuroleptic profile like clozapine and an anxiolytic profile like diazepam.

In the stress-induced hyperthermia- and the elevated plus-maze paradigm in mice [Lecci et al., Psychopharmacology 101:255–261 (1990) and Rodgers R. J. Behav. Pharmacol. 8: 477–496 (1998), respectively] the agents of the invention reduced the increase in body-temperature and increased the time spent on the open arms, respectively. They are therefore indicated for the treatment of anxiety disorders and panic disorders.

However, in contrast to benzodiazepines, the compounds of the invention do not impair memory as measured in the passive avoidance test, a paradigm in which memory formation impairment e.g. by benzodiazepines, glutamate NMDA receptor antagonists or muscarinic antagonists (Venable N; Kelly PH, Psychopharmacology; 1990: 100, 215–21) have been detected.

At doses of about 0.3 to 3 mg/kg p.o., the agents of the invention increase exploratory behaviour of mice in the open half of the half enclosed platform, a model which is predictable for anxiolytic activity (Psychopharmacology, 1986, 89:31–37). In the same half enclosed platform model, the agents of the invention, at the doses indicated above, also increase vigilance of the mice.

The compounds are therefore indicated for the treatment of depression, schizophrenia and dementia, in particular of senile dementia of the Alzheimer type (SDAT).

The agents of the invention at 0.03–3 mg/kg p.o. enhance learning/mlmory in mice as measured in the social recognition test similar to oxiracetam or $GABA_B$ blockers (Thor D. H. and Holloway W. R. J. Comp. Physiol. Psychol. 1982; 96: 1000–1006. Mondadori C. et al., Behavioural Brain Research 1996, 77: 227–229). Further, the agents at 0.03–0.3 mg/kg p.o. significantly Increased both recognition and discrimination indices in rats in a non-social situation using the object recognition test (ORT, Ennaceur A and Delacour J. Behav Brain Res 1988; 31: 47–59), similar to rivastigmine (Exelon®).

The compounds are therefore indicated for the treatment of cognitive disturbances and learning/mlmory disorders.

The positive effects on memory acquisition/retention combined with the soclotropic components displayed by the agents of the invention, suggest that these will prove useful in the treatment of ADHD and various types of dementias, including Alzheimers disease.

Furthermore at said acute doses the agents of the invention increase aggressive behaviour (attacks, chases, bites) in the Matched Pairs Situation test in mice [Dixon et al., J. Clin. Psychiatry 1994: 55: (9) [Suppl. B] 4–7]. Since as mentioned above they additionally attenuate defensive behaviours in the intruder mouse test, the agents of the invention exhibit an ethopharmacological profile which is very similar to that of clozapine and to some extent to that of antimanic agents (lithium, carbamazepine, valproate). They are therefore indicated for the treatment of affective disorders including bipolar disorders e.g. manic-depressive psychoses, extreme psychotic states e.g. mania, schizophrenia, and excessive mood swings where behavioural stabilisation is desired. In addition, the compounds are indicated in anxiety states, generalised anxiety as well as social stress and agoraphobia, as well as those behavioural states characterised by social withdrawal e.g. negative symptoms [Dixon A. K. Brit. J. Med. Psychol. 71: 417–445; Dixon A. K., Fisch H. U. Neuroscience and Biobehavioural Reviews. 1990: 23; 345–358] and post traumatic stress disorders.

The agents of the invention show antidepressant-like effects in the rat, similar to desipramine or fluoxetine when given subchronically (10–30 mg/kg, p.o.) in the forced swim test. (Porsolt, R. D. et al. Nature. 1977: 266, 730–732) and also produce antidepressant-like effects in the mouse, similar to fluoxetine (Porsolt, R. D. et al. Nature 1977: 266, 730–732). Finally, these agents, when given once per day for 14 days, (0.3–30 mg/kg p.o.), reverse both the characteristic hyper-reactivity of bulbectomised rats when first placed in a novel and stressful environment and the total activity, similar to imipramine and desipramine. (Song C and Leonard BE. Hum. Psychopharmacol 1994; 9: 135–146).

Collectively, this set of data suggests strong antidepressant potential for the agents of the invention. Combined with the aforementioned effects, the agents of the invention are indicated for uni-and bipolar depressive disorders, generalised anxiety disorders, post traumatic stress disorders, social phobia and anxiety, panic attacks, aggression, premenstrual dysphoria and autism, ADHD (attention deficit and hyperactivity disorders), schizophrenia, including negative symptoms, neurodegenerative diseases such as learning/mlmory disorders, dementias associated with various neurological disorders, age-associated memory impairment, and SDAT.

The agents of the invention are also effective In the treatment of various kinds of tumours, particularly of $sst_3$ receptor bearing tumours, as indicated in proliferaton tests with various different cancer cell lines and in tumour growth experiments in nude mice with hormone dependent tumours [see for example: G. Weckbecker et al., Cancer Research 1994, 54: 6334–6337]. Thus, the compounds are indicated In the treatment of, for example, cancers of the breast, the prostate, the colon, the pancreas, the brain and the lung (small cell lung cancer) and for In vivo imaging of $sst_3$ receptor bearing tumours.

For all the above mentioned indications, the appropriate dosage will of course vary depending upon, for example, the compound employed, the host, the mode of administration and the nature and severity of the condition being treated. However, In general, satisfactory results In animals are indicated to be obtained at a daily dosage of from about 0.1 to about 10 mg/kg animal body weight. In larger mammals, for example humans, an indicated daily dosage is in the range from about 5 to about 200 mg, preferably about 10 to about 100 mg of the compound conveniently administered in divided doses up to 4 times a day or in sustained release form.

The agents of the invention may be administered in free form or in pharmaceutically acceptable salt form. Such salts may be prepared in conventional manner and exhibit the same order of activity as the free compounds.

Accordingly in a further aspect the present invention provides the agents of the invention for use as pharmaceuticals, more specifically for treatment in the above-mentioned conditions, e.g. schizophrenia, depression, anxiety and bipolar disorders.

The present invention furthermore provides a pharmaceutical composition comprising an agent of the invention in association with at least one pharmaceutically acceptable diluent or carrier. Such compositions may be formulated In conventional manner. Unit dosage forms contain, for example, from about 0.25 to about 50 mg of an agent according to the invention.

Agents of the invention may be administered by any conventional route, for example parenterally e.g. in form of injectable solutions or suspensions, or enterally, preferably orally, e.g. in the form of tablets or capsules.

The agents of the invention may alternatively be administered e.g. topically in the form of a cream, gel or the like, or by inhalation, e.g. in dry powder form.

Examples for compositions comprising an agent of the Invention include, e.g. a solid dispersion, an aqueous solution, e.g. containing a solubilising agent, a microemulsion and a suspension of an agent of the invention. The composition may be buffered to a pH in the range of e.g. from 3.5 to 9.5, by a suitable buffer.

The agents of the invention can be administered either alone or in combination with other pharmaceutical agents effective in the treatment of conditions mentioned above.

Thus, the agents of the invention can be used for the treatment of depressive symptoms in combination with: tricyclics, MAO inhibitors, SSRI's, SNRI's, NK receptor antagonists, CRF-receptor antagonists, $5HT_7$ receptor-antagonists, mGlu receptor agonists/antagonist/modulators, $GABA_A$ or $GABA_{A/B}$ receptor agonist/antagonists or modulators, vasopressin receptor antagonists, electroconvulsive shock, sleep deprivation, or herbal medicine such as St. John's Worth.

The agents of the invention can also be used for the treatment of anxiety-symptoms in combination with: benzodiazepines including mitochondrial benzodiazepine-ligands, $5\text{-}HT_{1A}$ receptor agonists, SSRI's, SNRI's, NIK receptor-antagonists, CRF receptor-antagonists, vasopressin receptor-antagonists, mGlu receptor agonists/antagonist/modulators, $GABA_A$ or $GABA_{A/B}$ receptor agonists-antagonists or modulators.

The agents of the invention can further be used for the treatment of any forms of dementia, including Alzheimer's disease (SDAT) in combination with: acetylcholine-esterase inhibitors, such as rivastigmine and donepezil, mixed acetylcholine/butyrylcholine esterase-inhibitors and nicotinic-alpha$_7$-receptor agonists.

Moreover the agents of the invention can be used for the treatment of psychotic symptoms, including positive and negative symptoms in schizophrenia and schizoid type syndromes in combination with: any typical or a typical antipsychotic, such as clozapine or haloperidol, and nicotinic-alpha$_7$-receptor agonists.

Furthermore the agents of the invention can be used for the treatment of bipolar disorders in combination with: any antimanic agent (e.g. Lithium, Carbamazepine, Valproate) or any a typical or typical antipsychotic.

The pharmaceutical compositions for separate administration of the combination partners and for the administration in a fixed combination, i.e. a single galenical composition comprising at least two combination partners according to the invention, can be prepared in a manner known per se and are thus suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application.

In particular, a therapeutically effective amount of each of the combination partners may be administered simultaneously or sequentially and in any order, and the components may be administered separately or as fixed combination.

Accordingly the invention also provides a combination comprising a therapeutically effective amount of an agent of the invention and a second drug substance, said second drug substance being for example for use in any of the particular indications hereinbefore set forth.

The preferred indications are schizophrenia (especially negative symptoms and cognitive impairment), depression, anxiety and affective disorders, including bipolar disorders, e.g. mania.

The preferred agent of the invention for the above-mentioned indications is the (R)-1,1-bis-ethoxymethyl-3-(4-phenyl-1H-imidazol-2-yl)-2,3,4,9-tetrahydro-1H-β-carboline, in free base or acid addition salt form. This compound shows strong affinity for $sst_3$ receptors (human receptor: pKd=8.69; mouse receptor: pKd=8.30) with a selectivity of more than 400 fold over other somatostatin receptors. In the social contact assay (rat), it increases dose dependently the duration of social contacts of the "intruder" towards the "resident" at 0.01–10 mg/kg p.o. (maximal amplitude at 0.3–3 mg/kg p.o.), similarly to a single dose of chlordiazepoxide of 5 mg/kg p.o. In the passive avoidance test at 0.1, 1 or 10 mg/kg p.o., in contrast to chlordiazepoxide at 20 mg/kg p.o., no impairment of memory formation is observed. In the social recognition test (mice), at doses between 0.03 and 3 mg/kg p.o., the compound produces a significant increase of social recognition of a familiar partner, which is indicative of enhancement of learning/mlmory. In the forced swim test (Porsolt), the immobility time is shortened by 30–45% on subchronic administration of 12.5–25 mg/kg p.o.

In accordance with the foregoing, the present invention also provides the use of an agent of the invention as a pharmaceutical, e.g. for the treatment of schizophrenia, depression, anxiety and bipolar disorders.

Moreover the present invention provides the use of an agent of the invention for the manufacture of a medicament for the treatment of any condition mentioned above, e.g. schizophrenia, depression, anxiety and affective disorders.

In still a further aspect the present invention provides a method for the treatment of any condition mentioned above, e.g. schizophrenia, depression, anxiety and bipolar disorders, in a subject in need of such treatment, which comprises administering to such subject a therapeutically effective amount of an agent of the invention.

The following examples illustrate the invention. The temperatures are given in degrees Celsius and are uncorrected.

EXAMPLE 1

(R)-1,1-Dibutyl-3-(4-pyridin-4-yl-1H-imidazol-2-yl)-2,3,4,9-tetrahydro-1H-β-carboline 1. 2-Bromo-1-pyridin-4-yl-ethanone Hydrobromide 2-Bromo-1-pyridin-4-yl-ethanone hydrobromide is prepared from 1-pyridin-4-yl-ethanone in 83% yield according to a known procedure (A. Taurins, A. Blaga, J. Heterocycl. Chem. 7, 1139 (1970)).

2. [(R)-2-(1H-indol-3-yl)-1-(4-pyridin-4-yl-1H-imidazol-2-yl)-ethyl]-carbamic Acid Tert Butyl Ester A solution of Boc-D-tryptophan (7.00 g, 23.0 mmol) and $Cs_2CO_3$ (7.49 g, 23.0 mmol) in DMF (85 ml) is stirred for 30 min at room temperature. 2-Bromo-1-pyridin-4-yl-ethanone hydrobromide (6.49 g, 23.0 mmol) is added and stirring is continued at room temperature for 1 h. The solvent is removed in vacuo, the residue Is resuspended in AcOEt, filtered over hyflo and evaporated. The resulting oil is taken up in xylene (290 ml), ammonium acetate (35.46 g, 460 mmol) is added and the mixture is heated for 2 h at 160° using a Dean-Stark trap. After cooling to room temperature, AcOEt (100 ml) is added and the solution is washed with sat. aq. $K_2CO_3$ solution and brine (100 ml each). The aqueous layers are reextracted with AcOEt (2×100 ml); the combined organic layers are dried over $Na_2SO_4$ and evaporated. MPLC (400 g silica gel, AcOEt:MeOH 95:5 to 90:10) yields 3.36 g (36%) of [(R)-2-(1 H-iundol-3-yl)-1-(4-pyridin-4-yl-1H-imidazol-2-yl)-ethyl]-carbamic acid tert-butyl ester (TLC: silica gel, toluene:ethanol 5:1, $R_f$=0.31).

3. (R)-2-(1H-indol-3-yl)-1-(4-pyridin-4-yl-1H-imidazol-2-yl)-ethylamine dihydrochloride

[(R)-2-(1H-indol-3-yl)-1-(4-pyridin-4-yl-1H-imidazol-2-yl)-ethyl]-carbamic acid tert-butyl ester (3.46 g, 8.58 mmol) is dissolved in a mixture of glacial acetic acid (99.5%, 25 ml) and conc. aq. HCl (37%, 2.5 ml) and the solution is stirred under argon at room temperature for 1 h. The resulting precipitate is filtered, washed with acetone and dried to give 3.04 g (94%) of (R)-2-(1H-indol-3-yl)-1-(4-pyridin-4-yl-1H-imidazol-2-yl)-ethylamine dihydrochloride (TLC: silica gel, toluene:ethanol:AcOH 4:4:1, $R_f$=0.18).

4. (R)-1,1-Dibutyl-3-(4-pyridin-4-yl-1H-imidazol-2-yl)-2,3,4,9-tetrahydro-1βl-carboline A mixture of the above amine dihydrochloride (1.200 g, 3.19 mmol) and 5-nonanone (0.544 g, 0.663 ml, 3.83 mmol) in n-butanol (20 ml) is refluxed at 135° for 4.5 h. Using a Dean-Strark trap, 2 ml of the solvent are distilled off, then stirring is continued at 135° for 2 h and at 100° for 15 h. After cooling to room temperature and evaporation of the solvent, AcOET (50 ml) is added and the solution is washed with sat. aq. $NaHCO_3$ solution (20 ml), the aqueous layer is reextracted with AcOEt (2×50 ml), the combined organic layers are dried over $Na_2SO_4$, filtered and evaporated. After MPLC (80 g silica gel, AcOEt:triethyl amine 95:5) and recrystallization from methanol:water (80:20) (R)-1,1-Dibutyl-3-(4-pyridin-4-yl-1H-imidazol 2-yl)-2,3,4,9-tetrahydro-1H-β-carboline (0.806 g, 59%) is obtained as a colourless crystalline solid (mp. 200–205°, TLC: silica gel, toluene:ethanol 5:1, $R_f$=0.42, ESI-MS: $[M+H]^+$=428.2).

The following compounds of formula I wherein $R_4$ and $R_5$ are hydrogen can be prepared in analogy to Example 1.

| Example | R1 | R2 | R3 | mp. (base) | $[M + H]^+$ |
|---|---|---|---|---|---|
| 2 | Pyridin-2-yl | Butyl | Butyl | 85–105° | 428.2 |
| 3 | Pyridin-3-yl | Butyl | Butyl | 224–229° | 428.2 |
| 4 | Pyrazin-2-yl | Butyl | Butyl | 243° | 429.2 |
| 5 | [1,2,4]Triazolo[1,5-α]pyridin-6-yl | Butyl | Butyl | n.d. | 468.2 |
| 6 | 2-Methyl-[1,2,4]triazolo[1,5-α]pyridin-6-yl | Butyl | Butyl | n.d. | 482.3 |
| 7 | Imidazo[1,2-α]-pyridin-6-yl | Butyl | Butyl | 262.5° | 467.3 |
| 8 | 2-Methyl-imidazo[1,2-α]pyridin-6-yl | Butyl | Butyl | 254–257° | 481.3 |
| 9 | Pyridin-4-yl | Ethoxymethyl | Ethoxymethyl | 132° | 432.1 |
| 10 | Phenyl | Ethoxymethyl | Ethoxymethyl | 92–95° | 431 |
| 11 | Phenyl | Cyclopropylmethyl | Cyclopropylmethyl | 84–89° | 423 |
| 12 | Pyridin-4-yl | Cyclopropylmethyl | Cyclopropylmethyl | 146–149 | 424 |
| 13 | Phenyl | 1-(2-Cyclohexyl-ethyl)-piperidin-4-yl | | 163–166° | 494.7 |
| 14 | Phenyl | 6,7,8,9-Tetrahydro-5H-benzocyclohepten-7-yl | | 80–85° | 445.5 |
| 15 | Phenyl | Tetrahydro-pyran-4-yl | | 183–186° | 385.5 |
| 16 | Phenyl | 3,3,5,5-Tetramethyl-cyclohexyl | | 101–106° | 439.6 |
| 17 | Phenyl | Cyclooctyl | | 95–100° | 411.5 |
| 18 | 6-Methoxy-pyridin-3-yl | Butyl | Butyl | 103–108° | 458.6 |
| 19 | 1-Methyl-6-oxo-1,6-dihydro-pyridin-3-yl | Butyl | Butyl | 175–180° | 574.7 |
| 20 | 2-Methoxy-pyridin-4-yl | Butyl | Butyl | 162–165° | 458.6 |
| 21 | 2-Phenyl-thiazol-4-yl | Butyl | Butyl | 95–100° | 510.7 |
| 22 | Benzo[1,2,5]thiadiazol-5-yl | Ethoxymethyl | Ethoxymethyl | 90–95° | 489.6 |
| 23 | Quinoxalin-6-yl | Ethoxymethyl | Ethoxymethyl | 110–116° | 483.6 |
| 24 | 1-Methyl-6-oxo-1,6-dihydro-pyridin-3-yl | Ethoxymethyl | Ethoxymethyl | 132–137° | 462.5 |

What is claimed is:

1. A compound of formula I

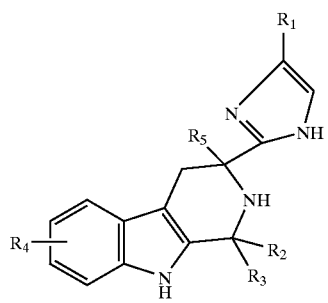

wherein

R₁ is a group of formula

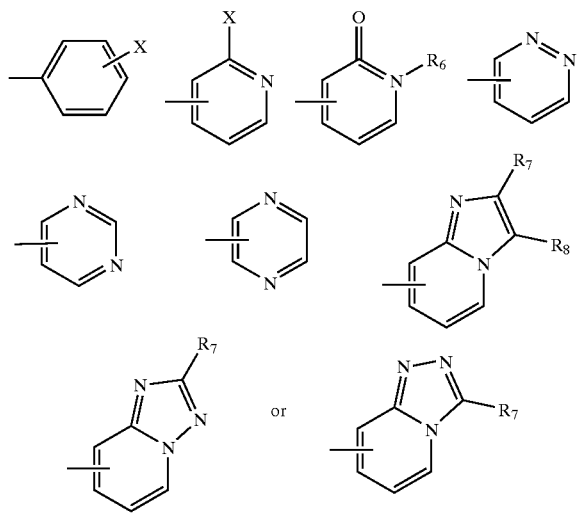

wherein $R_6$ is $(C_{1-4})$alkyl, $R_7$ and $R_8$, independently, are hydrogen or $(C_{1-4})$alkyl and X is hydrogen, $(C_{1-4})$alkoxy, $(C_{1-4})$alkylamino or di$(C_{1-4})$alkylamino, $R_2$ and $R_3$, independently, are $(C_{1-4})$alkoxy$(C_{1-4})$alkyl or $(C_{3-7})$cycloalkyl$(C_{1-4})$alkyl, or, provided $R_1$ is not an optionally substituted phenyl group, $(C_{1-12})$alkyl, $R_4$ is hydrogen, $(C_{1-4})$alkyl, $(C_{1-4})$alkoxy, halogen or trifluoromethyl and $R_5$ is hydrogen or $(C_{1-4})$alkyl, in free base or acid addition salt form.

2. The compound according to claim 1 which is (R)-1,1-bis-ethoxymethyl-3-(4-phenyl-1H-imidazol-2-yl)-2,3,4,9-tetrahydro-1H-β-carboline, in free base or acid addition salt form.

3. A process for the preparation of a compound of formula I as defined in claim 1, or a salt thereof, which comprises reacting a compound of formula II

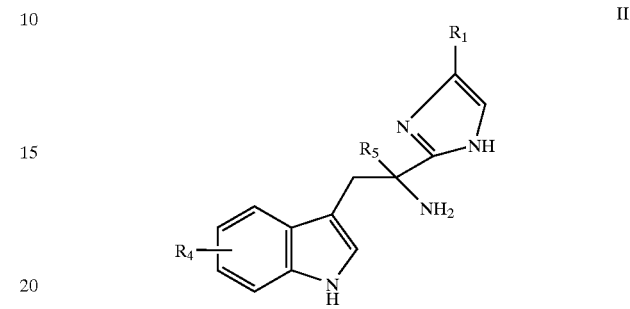

wherein $R_1$, $R_4$ and $R_5$ are as defined in claim 1, with a compound of formula III

wherein $R_2$ and $R_3$ are as defined in claim 1, and recovering the resulting compound of formula I in free base or acid addition salt form.

4. A pharmaceutical composition comprising a compound of claim 1 in free base of pharmaceutically acceptable acid addition salt form, in association with a pharmaceutical carrier or diluent.

5. A combination comprising a therapeutically effective amount of a compound of claim 1 in free base or pharmaceutically acceptable acid addition salt form and a second drug substance, for simultaneous or sequential administration.

6. A method for the treatment of depression, anxiety and bipolar disorders in a subject in need of such treatment, which comprises administering to such subject a therapeutically effective amount of a compound of claim 1 in free base or pharmaceutically acceptable acid addition salt form.

* * * * *